United States Patent
Cawthon et al.

(10) Patent No.: US 7,762,524 B2
(45) Date of Patent: Jul. 27, 2010

(54) BARRIER ASSEMBLY FOR USE WITH NEEDLELESS CONNECTOR

(75) Inventors: Dustin C. Cawthon, Crystal Lake, IL (US); Birendra K. Lal, Palatine, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 33 days.

(21) Appl. No.: 12/254,366

(22) Filed: Oct. 20, 2008

(65) Prior Publication Data

US 2010/0100056 A1    Apr. 22, 2010

(51) Int. Cl.
F16L 37/28 (2006.01)

(52) U.S. Cl. .............. 251/149.6; 604/533; 604/537; 251/149.1; 251/341

(58) Field of Classification Search .............. 251/149.1, 251/149.6, 341; 604/533–538
See application file for complete search history.

(56) References Cited

U.S. PATENT DOCUMENTS

| | | | | |
|---|---|---|---|---|
| 5,269,771 | A * | 12/1993 | Thomas et al. | 604/539 |
| 5,492,147 | A * | 2/1996 | Challender et al. | 137/614.05 |
| 5,492,304 | A * | 2/1996 | Smith et al. | 251/149.1 |
| 5,509,433 | A | 4/1996 | Paradis | |
| 5,792,120 | A | 8/1998 | Menyhay | |
| 6,113,068 | A * | 9/2000 | Ryan | 251/149.4 |
| 6,575,960 | B2 * | 6/2003 | Becker et al. | 604/533 |
| 6,994,315 | B2 * | 2/2006 | Ryan et al. | 251/149.6 |
| 7,396,051 | B2 * | 7/2008 | Baldwin et al. | 285/354 |
| 2005/0147524 | A1 | 7/2005 | Bousquet | |
| 2006/0189961 | A1 * | 8/2006 | Miyahara | 604/535 |
| 2006/0192164 | A1 * | 8/2006 | Korogi et al. | 251/149 |
| 2006/0222845 | A1 * | 10/2006 | Deng et al. | 428/336 |
| 2008/0027410 | A1 | 1/2008 | Harding et al. | |
| 2008/0033371 | A1 | 2/2008 | Updegraff et al. | |

FOREIGN PATENT DOCUMENTS

| | | |
|---|---|---|
| WO | WO 97/24548 | 7/1997 |
| WO | WO 2007/056363 | 5/2007 |
| WO | WO 2008/011581 | 1/2008 |

OTHER PUBLICATIONS

Extended European Search Report for corresponding European Application No. 09252450.3, dated Feb. 8, 2010 (6 pages).

* cited by examiner

*Primary Examiner*—John K Fristoe, Jr.
*Assistant Examiner*—Marina Tiet Jen
(74) *Attorney, Agent, or Firm*—Marshall, Gerstein & Borun LLP (57) ABSTRACT

A needleless valve assembly includes a needleless connector having a housing with an inlet end with an inlet opening and an outlet end with an outlet opening, and a valve disposed in the housing to control passage between the openings. The assembly also includes a collar having an exterior surface and an interior surface, and a first end with a collar opening communicating between the interior surface and the exterior surface and a second end moveably attached to the housing. Further, the assembly includes a barrier disposed across the collar opening with a slit therethrough and including an antimicrobial material. The collar is moveable relative to the housing so that the inlet end of the housing depends past the exterior surface of the collar through the slit in the barrier. A kit may include the assembly and a catheter having a first end attached to the outlet opening.

24 Claims, 5 Drawing Sheets

BARRIER ASSEMBLY FOR USE WITH NEEDLELESS CONNECTOR

BACKGROUND

This patent is directed to a barrier assembly for use with a needleless connector, and, in particular, to a barrier assembly for use with a needleless connector wherein the barrier assembly includes a moveable collar and an anti-microbial material.

Intravenous ("I.V.") therapy involves the delivery of fluids to a patient through a vein. For example, a catheter is placed into the vein of the patient, and then fluids are administered to the patient through the catheter. Typically, the catheter is connected to an administration set in communication with a container, such as a flexible container or bag, from which fluids are infused into the patient.

One way in which the catheter has been attached to the administration set is through the use of needleless connectors. Needleless connectors reduce the risk of accidental sharps injuries to the patient and the healthcare worker. One common type of needleless connector is the Luer-activated valve or device. Another common type is the slit septum, which utilizes a cannula or other non-Luer connector to access the device.

However, because needleless connectors are in direct communication with the patient's vascular system, bypassing the body's natural defenses to microbial invasion, caution must be exercised to prevent device-related bloodstream infections. Bloodstream infections may not only prolong hospital stays, increasing costs, but may cause serious complications for the patient, potentially resulting in death. The likelihood and severity of the infection may be greater given that I.V. therapies are conventionally used with patients whose health is already compromised, and may even be immuno-compromised.

One approach to minimizing contamination has been to employ a recessed valve with a sterile protective cap, which is placed over the valve to prevent microbial contamination. The cap must be replaced with a new sterile cap each time the valve is accessed. Additionally, certain protocols require that the cap be replaced periodically as well. This approach is costly in terms of material and time required, and actually may present additional opportunities for contamination to occur because the caps can become inadvertently contaminated through routine handling, where organisms are transferred from the skin or other contaminated surfaces.

Another approach has been to make the valve flush with the surface to be accessed. The surface may then be disinfected prior to access, typically with isopropyl alcohol, povidone iodine, or chlorhexidine. Proper technique usually requires adequate contact and drying time so as to prevent asepsis. However, proper technique is not always possible, because of the need to administer emergency care on a time critical basis, for example, and because even perfect technique may not reach crevices or interstitial spaces that are difficult or impossible to disinfect.

A still further approach has been to provide a cap that includes a pad soaked in a disinfectant, which cap is detachable from the connector or tethered to the connector by a harness. During times when the connector is not in use, the cap is placed over the valve to prevent contamination. It is suggested that the contact between the pad and the valve causes the valve to be bathed in the disinfectant between uses. However, because the cap is detached from the valve, it remains possible for the cap not to be properly replaced after use of the valve. Further, removal of the cap and its placement on a surface or its dangling from the connector can expose the cap to contamination, such as in the form of colonizing pathogens or general particulate. The colonizing pathogens introduced through inadvertent contamination of the cap may overwhelm the antimicrobial agent, allowing the pathogens to be transferred to the needleless connector. The particulate contamination would not be affected by the antimicrobial agent, and may be transferred to the connector as well.

As set forth in more detail below, the present disclosure sets forth an improved assembly embodying advantageous alternatives to the conventional devices discussed above.

SUMMARY OF THE INVENTION

In one aspect, a needleless valve assembly includes a needleless connector having a housing with an inlet end with an inlet opening and an outlet end with an outlet opening, and a valve disposed in the housing to control passage between the inlet opening and the outlet opening. The assembly also includes a collar having an exterior surface and an interior surface, and a first end with a collar opening communicating between the interior surface and the exterior surface and a second end moveably attached to the housing. Further, the assembly includes a barrier disposed across the collar opening with a slit therethrough and including an anti-microbial material. The collar is moveable relative to the housing between a first position with the barrier abutting the inlet end of the housing, and a second position with the inlet end of the housing depending past the exterior surface of the collar through the slit in the barrier.

According to another aspect, a kit includes a needleless valve assembly and a catheter. The needleless valve assembly includes a needleless connector having a housing with an inlet end with an inlet opening and an outlet end with an outlet opening, and a valve disposed in the housing to control passage between the inlet opening and the outlet opening. The assembly also includes a collar having an exterior surface and an interior surface, and a first end with a collar opening communicating between the interior surface and the exterior surface and a second end moveably attached to the housing. Further, the assembly includes a barrier disposed across the collar opening with a slit therethrough and including an anti-microbial material. The collar is moveable relative to the housing between a first position with the barrier abutting the inlet end of the housing, and a second position with the inlet end of the housing depending past the exterior surface of the collar through the slit in the barrier. The catheter has a first end attached to the outlet opening of the housing of the needleless connector.

Additional aspects of the disclosure are defined by the claims of this patent.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

Figure 1:
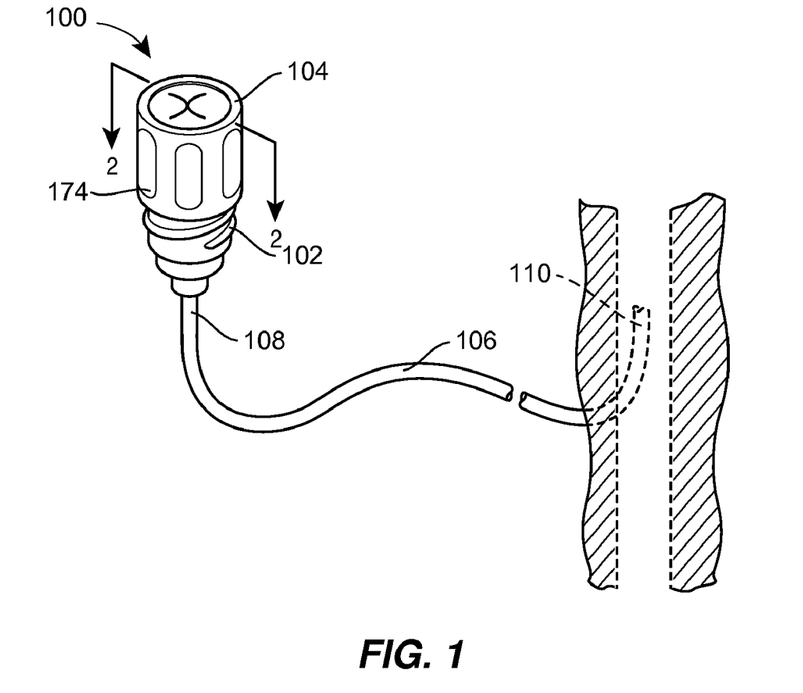
FIG. 1 is a perspective view of a combination of a needleless valve assembly according to the present disclosure and a catheter.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph FIG. 1 illustrates a needleless valve assembly 100 including a needleless connector 102 with a moveable collar 104 attached thereto. As shown, a catheter 106 has a first end 108 attached to the needleless connector 102, and a second end 110 introduced into the vein of a patient. While the needleless valve assembly 100 according to the present disclosure is illustrated with respect to a particular use (i.e., with the connector 102 attached directly to the catheter 106), it will be recognized that a number of other uses are possible, as explained in greater detail below.

Figure 2:
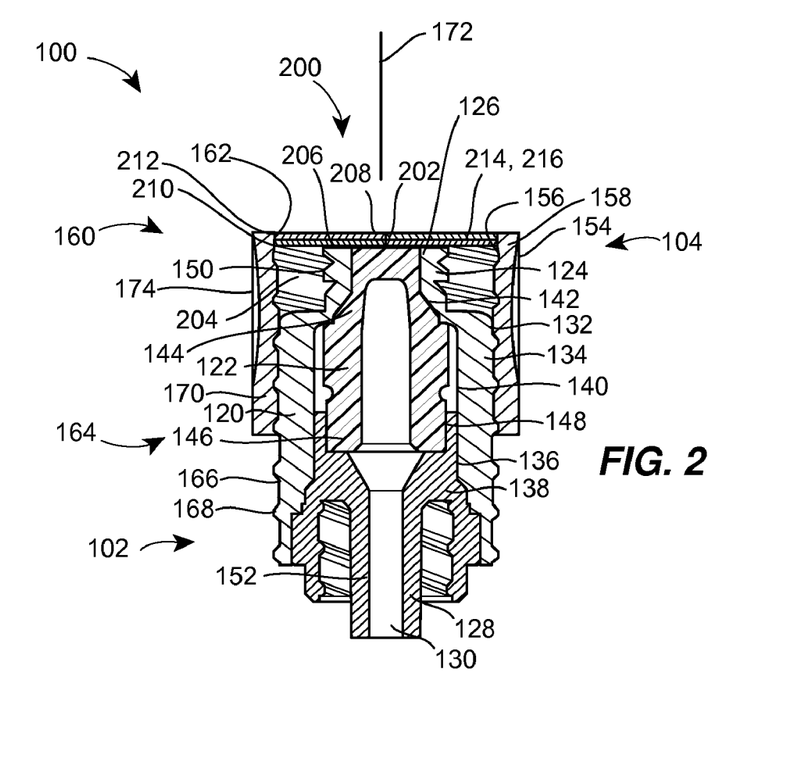
FIG. 2 is a cross-sectional view of the needleless valve assembly according to FIG. 1 taken about line 2-2, with the collar in a first position.
Figure 3:
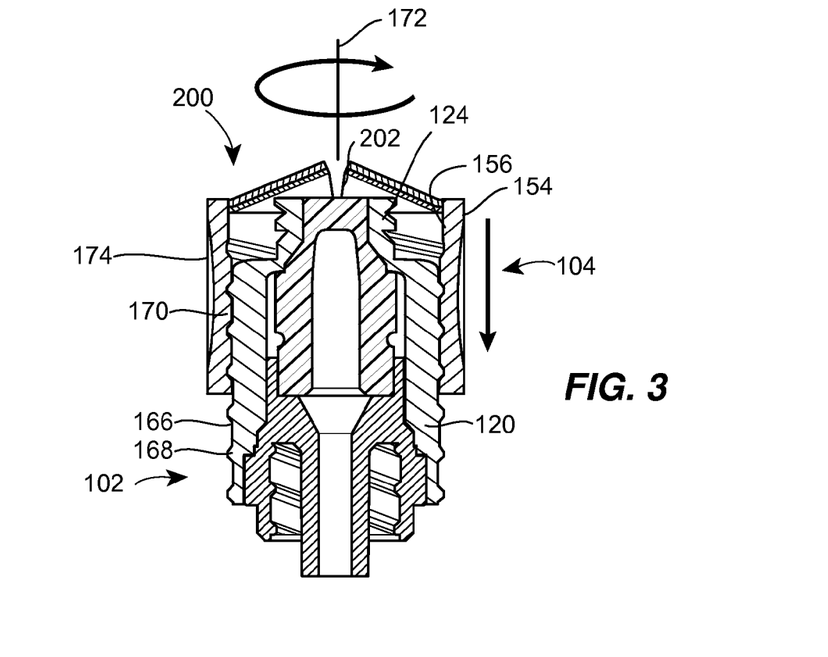
FIG. 3 is a cross-sectional view of the needleless valve assembly according to FIG. 1, with the collar in an intermediate position.
Figure 4:
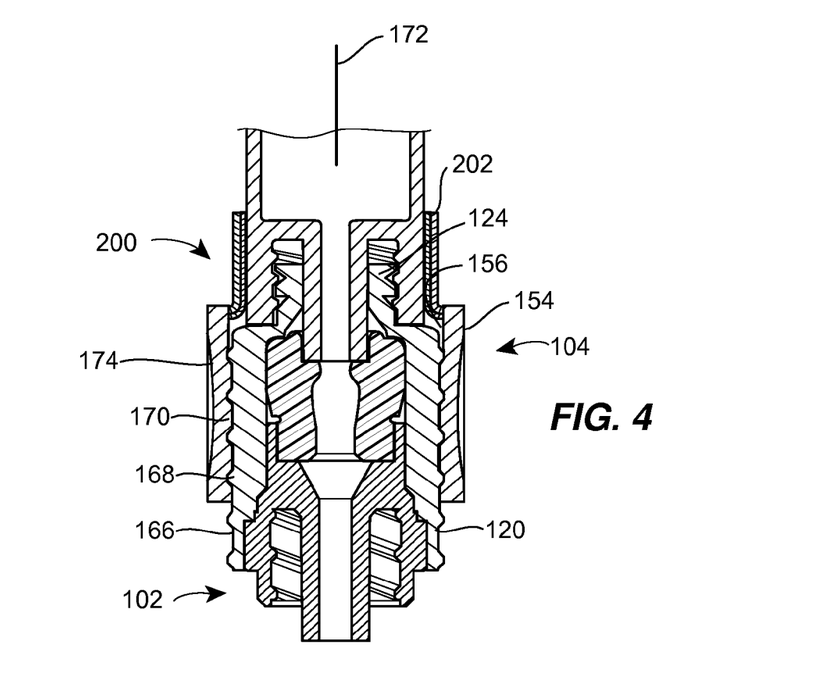
FIG. 4 is a cross-sectional view of the needleless valve assembly according to FIG. 1, with the collar in a second position.

The embodiment of the needleless valve assembly 100 illustrated in FIG. 1 is also shown in FIGS. 2-4. Further embodiments of the needleless valve assembly 100 are illustrated in FIGS. 5-9. It will be recognized that many of the features of these embodiments may be combined, despite their presentation in the illustrations directed to the different embodiments. Also, similar reference numerals have been used for similar structures in different embodiments, with the use of primes to differentiate between the similar structures in the different embodiments.

As best seen in FIG. 2, the needleless connector 102 used in the needleless valve assembly 100 according to the present disclosure includes a housing 120 and a valve 122. As illustrated, the needleless connector 102 is in the form of a Luer-activated valve. However, it will be recognized that aspects of the present disclosure may be used with other needleless connectors. For example, aspects of the present disclosure may be used instead with a needleless connector using a slit septum instead of a Luer-activated valve.

The housing 120 has an inlet end 124 with an inlet opening 126 and an outlet end 128 with an outlet opening 130. In particular, the housing 120 has an inlet section 132 that includes a wall 134 through which the inlet opening 126 is formed, and an outlet section 136 that includes a wall 138 through which the outlet opening 130 is formed. The inlet section 132 also has an interior surface 140 that defines a valve seat 142.

The valve 122 is disposed in the housing 120 with a first end 144 abutting the valve seat 142. The valve 122 also has a second end 146 that abuts the outlet section 136; as shown, a stepped region 148 is provided to receive the second end 146 of the valve 122. The valve 122 is disposed in the housing 120 between the inlet and outlet sections 132, 136 to control passage between the openings 126, 130.

The inlet section 132 and the outlet section 136 both have mechanisms for joining the needleless connector 102 to other devices. For example, the inlet section 132 has an exterior surface 150 that is threaded at or near the inlet end 124 to accept a male Luer lock, for example (see FIG. 4). Similarly, the outlet section 136 has a lumen 152 to which the catheter 106 may be attached to place the needleless connector 102 in fluid communication with the patient.

As mentioned above, the needleless valve assembly 100 according to the present disclosure also includes the collar 104. The collar 104 has an exterior surface 154 and an interior surface 156. As illustrated, the collar 104 is in the form of a cylinder, although the shape may vary, both relative to the exterior surface 154 and the interior surface 156, and thus relative to the thickness and shape of a wall 158 that defines the exterior and interior surfaces 154, 156. The collar 104 has a first end 160 with a collar opening 162 communicating between the interior surface 156 and the exterior surface 154 and a second end 164 moveably attached to the housing 120.

Figure 5:
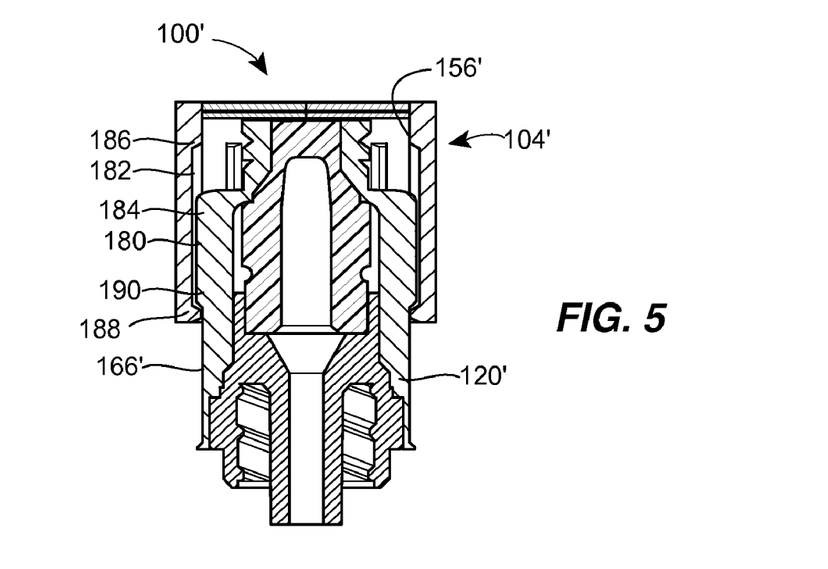
FIG. 5 is a cross-sectional view of another embodiment of the needleless valve assembly according to the present disclosure, having a different moveable attachment.

The moveable attachment of the second end 164 of the collar 104 to the housing 120 may be achieved using a variety of mechanisms, only two of which are illustrated herein. FIGS. 1-4 illustrate an embodiment wherein mating threaded sections of the housing 120 and collar 104 provide the moveable attachment wherein the housing 120 and collar 104 move axially relative to each other as well as rotate about a common axis. FIG. 5 illustrates another embodiment wherein a shoe or tab formed on the exterior surface of the housing 120' mates with a track or groove formed on the interior surface of the collar 104', and the housing 120' and collar 104' move axially without rotation. It will be recognized, for example, that while the tracks or grooves are aligned parallel to an axis of the housing 120' and collar 104' in FIG. 5, it would also be possible for the tracks or grooves to be helical instead, providing for axial and rotational motion.

Turning then to FIGS. 2-4, the housing 120 has an exterior surface 166 with a threaded section 168. Similarly, the interior surface 156 of the collar 104 has a threaded section 170. The threaded section 168 of the housing 120 engages the threaded section 170 of the collar 104. The collar 104 may be grasped about its exterior surface 154 to rotate the collar 104 about a common axis 172 of the collar 104 and the housing 120, and thus move the collar 104 axially relative to the housing 120. Indentations 174 may be provided in the exterior surface 154 of the collar 104 to permit the user to better grip the collar 104, although the indentations 174 are not necessary for proper functioning of the assembly 100.

By contrast, FIG. 5 illustrates an embodiment wherein the housing 120' and the collar 104' have first and second facing surfaces, in particular the exterior surface 166' of the housing 120' and the interior surface 156' of the collar 104'. The assembly 100' also includes a shoe 180 attached to the first facing surface and a race 182 formed in the second facing surface. In the embodiment, illustrated the shoe 180 is attached to the exterior surface 166' of the housing 120', while the race 182 is formed in the interior surface 156' of the collar 104', although it could as easily have been reversed instead. The shoe 180 is disposed in the race 182, and the cooperation of the shoe 180 and the race 182 moveably attaches the collar 104' to the housing 120' and guides the motion of the collar 104' relative to the housing 120'.

It will be recognized that the motion of the shoes 180 in the races 182, and thus the collar 104' relative to the housing 120', in one axial direction is limited by the abutment of a first end 184 of the shoe 180 with the first end 186 of the race 182. To limit the motion of the collar 104' relative to the housing 120' in the opposite axial direction, the race 182 may have a second end 188 that abuts a second end 190 of the shoe 180. The second end 188 of the race 182 may be formed as one piece with the remainder of the collar 104', as shown, or the collar 104' may be formed in two pieces, with the first piece defining the race 182 except for the second end 188 and with the second piece defining the second end 188, the two pieces being joined together to form the collar 104'.

In fact, according to certain embodiments of the present disclosure, a biasing mechanism, like a resilient member or spring, may be disposed between various structures of the moveable attachment to bias the collar and the housing to the first, or rest, position. For example, a resilient member or spring may be disposed between the first end 184 of the housing 120' and the first end 186 of the race 182 of the collar 104'. Movement of the collar 104' relative to the housing 120' would compress the resilient member thus disposed, and would thus provide the return force necessary to return the assembly 100' to the rest position shown in FIG. 5.

Returning then to FIGS. 1-4, in addition to the needleless connector 102 and the collar 104, the needleless valve assembly 100 also includes a barrier 200. The barrier 200 is disposed across the collar opening 162 with a slit 202 therethrough. The barrier 200 includes an antimicrobial material, and is intended to prevent contamination of the needleless connector 102, particular at its inlet end 124. The barrier 200, the collar 104 and the housing 120 bound a space 204, which is referred to herein as the collar space.

As shown in FIGS. 2-4, the collar 104 is moved relative to the housing 120 between a first, or rest, position and a second, or operational, position. In the first position, as illustrated in FIG. 2, the barrier 200 abuts the inlet end 124 of the housing 120. As the collar 104 is moved relative to the housing 120, as illustrated in FIG. 3, the inlet end 124 of the housing 120 pushes on the barrier 200, and passes through the slit 202 in the barrier 200. FIG. 4 illustrates the collar 104 in the second position, with the inlet end 124 of the housing 120 depending past the exterior surface 154 of the collar 104 through the slit 202 in the barrier 200 and in combination with a male Luer connector.

Figure 7:
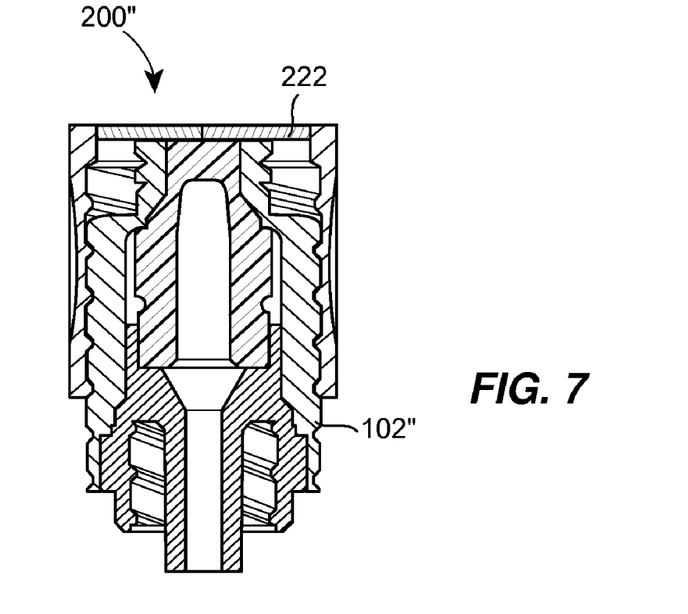
FIG. 7 is a cross-sectional view of a still further embodiment of the needleless valve assembly according to the present disclosure, having a single-layer barrier.
Figure 8:
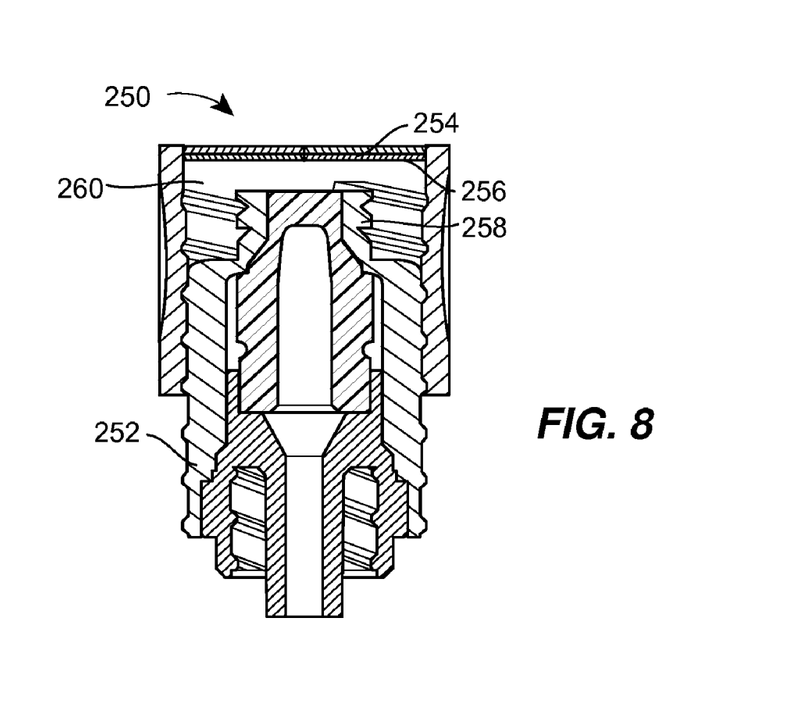
FIG. 8 is a cross-sectional view of another embodiment of the needleless valve assembly according to the present disclosure, wherein the barrier is initially spaced from an inlet end of the associated connector.
Figure 9:
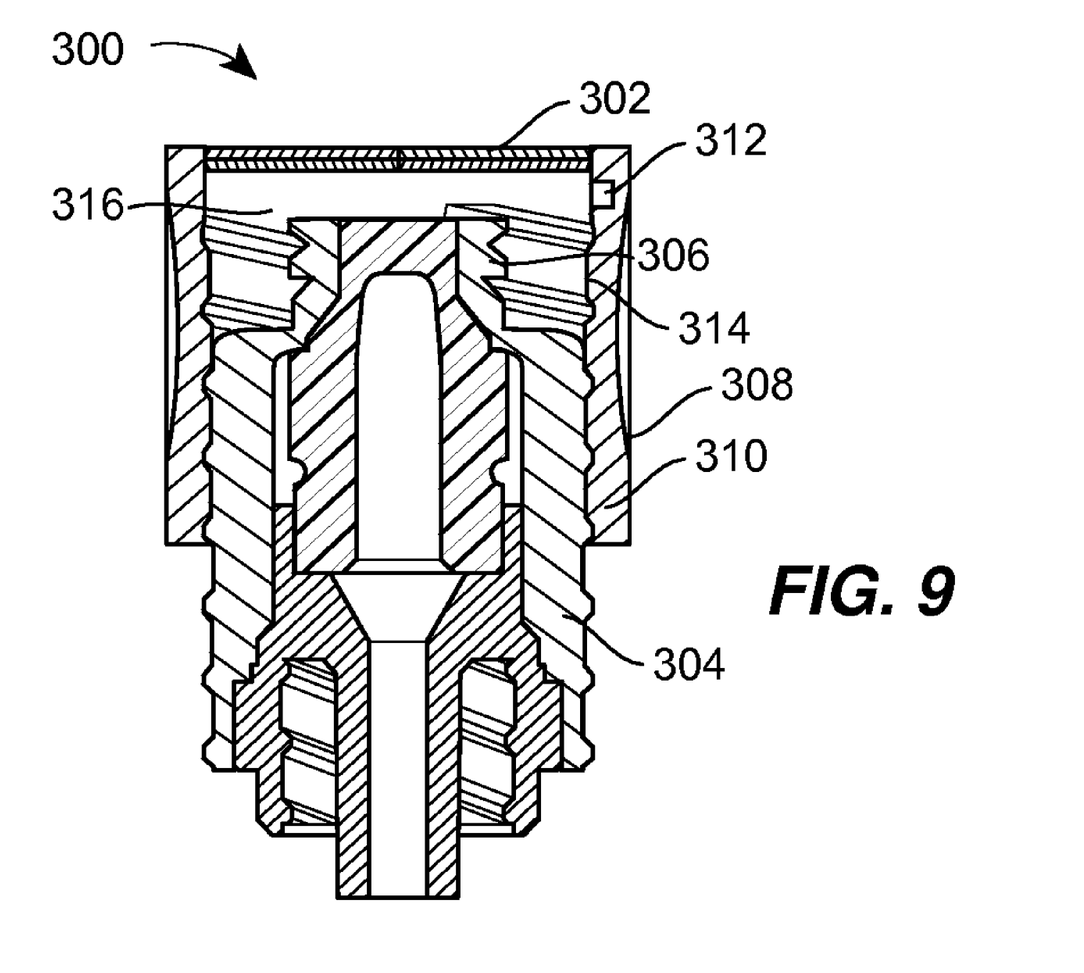
FIG. 9 is a cross-sectional view of an embodiment of the needleless valve assembly incorporating a radiation source.

The barrier may take a variety of forms, some exemplary embodiments of which are illustrated. For example, the barrier may include two layers, as illustrated in FIGS. 1-6, 8 and 9, or only a single layer, as illustrated in FIG. 7; the barrier could also include more than two layers for that matter. The barrier may abut the end of the connector, or may be disposed spaced apart from the inlet end of the connector, as illustrated in FIGS. 8 and 9.

Turning first to FIGS. 1-5, a two-layer embodiment of the barrier 200 is illustrated. As mentioned above, a first layer 206 is disposed proximal to the inlet end 124 and includes the antimicrobial material, while a second layer 208 is disposed distal to the inlet end 124. The layers 206, 208 are joined at their peripheries 210, 212 to the interior surface 156 of the collar 104, although this need not be the case according to all embodiments (see, for example, the embodiment of FIG. 6). The slit 202 passes through the first and second layers 206, 208 at substantially the same location.

The first and second layers 206, 208 may be made of different materials, and thus provide different functions relative to the assembly 100.

For example, the first layer 206 may be made from a material having pores, the antimicrobial material disposed in the pores. The pores may be large, and the material thus may have the appearance of a sponge. However, the pores may be microscopic, and thus the material may not appear appreciably different from other polymeric materials. In either event, the purpose of the first layer 206 may be to act as a carrier for the antimicrobial material.

The second layer 208, by contrast, may be made of a material that acts in conjunction with the first layer 206 to provide additional protections. For example, where the first layer 206 is porous like a sponge, the first layer 206 may not present sufficient resistance to penetration of foreign objects past the barrier 200. The second layer 208 may provide additional stiffness to the barrier 200 to increase resistance to penetration of an objection. The second layer 208 could also provide a barrier to liquids or gases, thereby keeping undesired materials out of the collar space 204, and/or keeping the desired materials, including the antimicrobial material, in the collar space 204.

The first and second layers 206, 208 abut each other as illustrated. This need not be the case according to all embodiments. For example, according to other embodiments, the two layers 206, 208 may be spaced from each other, such that there is a region between the first layer 206 and the second layer 208 unoccupied by either layer 206, 208. As such, when the collar 104 is moved relative to the housing 120, the inlet end 124 will first pass through the first layer 206, and then through and past the second layer 208.

In the alternative to the spaced arrangement of the first and second layers 206, 208, more than two layers may be used, such that the first and second layers 206, 208 discussed above are separated by one or more intermediate layers rather than simply empty space. That is, the first layer 206 may still lie proximal to the inlet end 124 and the second layer 208 may still lie distal to the inlet end 124, but an intermediate layer may be disposed between the first and second layers 206, 208, such that the first and second layers 206, 208 abut the intermediate layer, instead of each other.

Figure 6:
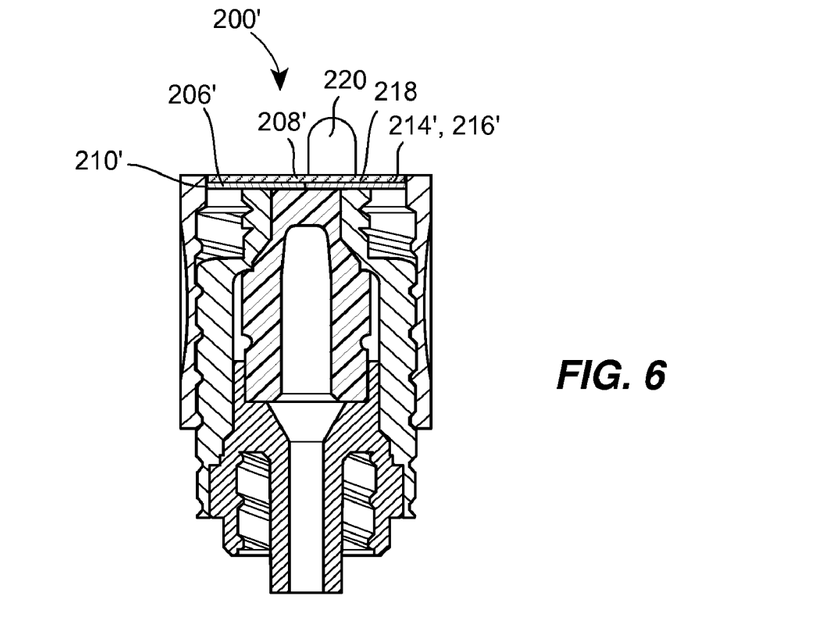
FIG. 6 is a cross-sectional view of a further embodiment of the needleless valve assembly according to the present disclosure, having a different two-layer barrier.

The first and second layers 206, 208 may be attached, as well as abutting. For example, the first and second layers 206, 208 may be formed separately and attached uniformly over facing surfaces 214, 216, or the first and second layers 206, 208 may be attached only at discrete points over the facing surfaces 214, 216. Alternatively, the second layer 208 may be deposited onto a surface 214 of the first layer 206, as a coating, for example.

Where the first and second layers are formed separately and attached, the attachment may be releasable, as illustrated in FIG. 6. As shown, the barrier 200' includes a second layer 208' is formed by a disc of material 218 that is releasably attached to a first layer 206' on facing surfaces 214' 216'. For example, a releasable adhesive may be used that is of sufficient strength to resist removal from incidental forces, but is not so firmly bonded as to prevent removal at the time of use. To facilitate removal, a pull tab 220 may be attached to or formed with the disc 218, which pull tab 220 may be grasped by the user. In this embodiment, while the first layer 206' may be attached to the collar 204' at its periphery 210', the second layer 208' need not be.

Regardless of the arrangement used, the first layer 206 typically will include the antimicrobial material. By illustration, and not by way of limitation, the antimicrobial material may be a chemical disinfectant or a vapor disinfectant. Illustrative examples from each group are provided as follows.

In regard to chemical disinfectants, these antimicrobial agents that can be incorporated into the materials of the first layer 206 to kill organism through contact with the first layer 206. In the alternative or in addition, these materials may be released from the first layer 206 onto the exterior surface 150 of the inlet end 124 of the housing 120, for example, as the inlet end 124 of the housing 120 passes through the barrier 200. In fact, the motion of the first layer 206 as the collar 104 moves between the first and second positions may act as a "pump" to cause material contained deeper in the first layer 206 to be drawn up to the surface of the first layer 206 over time.

Chemical disinfectants may include alcohols, such as isopropanol and ethanol. Biguanides may also be used, including chlorhexidine and its salts (e.g. chlorhexidine acetate, chlorhexidine gluconate, chlorhexidine hydrochloride and chlorhexidine sulfate). Further examples include, bisphenols, including triclosan, and halogen-releasing agents, including chlorine and iodine compounds. Silver and its salts (e.g. silver acetate, silver iodide, silver nitrate, silver sulfadiazine) may be included, as may copper and its salts. As a further alternative, quaternary ammonium compounds, including benzalkonium chloride, may be used. Still further exemplary alternatives include antimicrobial dyes, including acridines and crystal violet, boric acid, salicylic acid and N-halamines.

In regard to vapor disinfectants, these antimicrobial agents may be incorporated into the materials of the first layer 206 to kill organisms by creating a biocidal vapor in the collar space 204. While a variety of materials may be used, exemplary materials include elemental iodine (vapor) and ozone.

Of course, as illustrated in FIG. 7, it is also possible to have an embodiment of the barrier 200" with only a single layer 222. According to such an embodiment, the single layer 222 may act as a carrier for the antimicrobial material, as well as limiting access to the connector 102". In fact, the single layer 22 may be manufactured to provide the function of a two layer barrier 200 with a single layer; for example, the single layer may be made porous on a first side proximal to the connector 102", so as to accept the antimicrobial material, and made non-porous on a second side distal to the connector 102", so as to limit the passage of liquids or gases past the barrier 200".

Further, as noted above, more than two layers may be used in the barrier. It may thus be possible to form a barrier that is a "sandwich" of layers, some of which may act as a carrier for an antimicrobial material and some of which may not. The layers that do not act as a carrier may act instead as a spacer, in the sense that these layers may act to prevent the antimicrobial materials from different carrier layers from passing or migrating between layers. By forming such a "sandwich" of layers it might be possible, for example, to have a carrier layer proximal-most to the first end of the housing, to form a vapor in the collar space, while having another carrier layer with a chemical disinfectant that "wipes" the first end of the housing as it passes through the slit in the barrier. Also, the additional layers may prevent ingress of particulate into the fluid path by filtering the fluid moving through the layers. Further alternatives will be recognized as well.

As a further alternative, as illustrated in FIG. 8, the barrier may be spaced from the inlet end of the connector. In this particular embodiment, a two-layer barrier 250 is used with a needleless connector 252. The inner layer 254 of the barrier 250 has a surface 256 that is initially spaced from an inlet end 258 of the connector 252, such that the inlet end 258 is disposed within the collar space 260. This arrangement may be particularly useful when using vapor disinfectants, such as the exemplary disinfectants listed above. However, it will be recognized that even this embodiment will have a first position wherein the inlet end 258 abuts the barrier 250 as the inlet end 258 is advanced in the direction of the barrier 250 from its initial position spaced from the barrier 250. It will also be recognized that the variants described above relative to those barriers that abut or contact the inlet end of the connector (e.g., relating to number of layers, slit shape and size, etc.) are equally applicable in regard to those embodiments were the barrier is initially spaced from the inlet end.

FIG. 9 illustrates a further application for the initially spaced barrier of FIG. 8. This assembly 300 includes a barrier 302 that is spaced from the connector 304, and in particular from an inlet end 306 of the connector 304. The barrier 302 is attached to a collar 308, which collar 308 has an wall 310. Attached to or embedded in the wall 310 of the collar 308 is a radiation source 312. For example, ultraviolet radiation could be generated by a small light emitting diode (LED) embedded within the collar wall 310, emitting radiation from an inner surface 314 of the collar wall 310 toward the inlet end 306 of the connector 304, and within the collar space 316 generally. The radiation source may have a power source that may be integral (i.e., made as one piece or unit) with the LED, or that may be otherwise attached to embedded in the wall 310 of the collar 308, or that may even be disposed exterior to the wall 310. Other mechanisms than the LED may be used as the radiation source as well.

As further examples of the possible variants to the barrier as illustrated, the shape and form of the slit in the barrier that permits passage through the barrier make take a variety of forms. As best seen in FIG. 1, the slit may have the form of a cross, when viewed from above. The cross may be formed, as illustrated, as the union of two arcuate cuts that join at the point furthermost from their respective ends. According to other embodiments, the cross may be defined by two intersecting straight-edge cuts, or the slit need not be a cross at all, but rather some other shape instead.

According to still other embodiments, the slit may not penetrate through all of the layers, or a slit may not be required at all. That is, according to an exemplary embodiment where a slit is not included through each of the layers, the second (or outer) layer may include a slit therethrough, while the first layer may be formed of a flexible and porous material that allows for fluid flow through the first layer when in a stressed (e.g., stretched) state. For example, the first layer may be defined by a septum having a plurality of pinholes, the pinholes being closed or sealed when the septum is in the unstressed (unstretched) state and being open when the septum is stressed (stretched) by the needleless connector and/or Luer tip to permit fluid flow. According to an exemplary embodiment where a slit is not included through any of the layers, the entire barrier may be comprised of a flexible and porous material that allows fluid flow in the stressed state. As an additional benefit, the material that defines the barrier according to such embodiments may act as a filter, preventing ingress of particulate material while allowing for fluid flow in the stressed state.

As also noted above, while the needleless valve assembly according to the present disclosure has been shown as part of a vascular or venous access device, the assembly is not limited to only such uses. It is believed that the needleless valve assembly may be used wherever needleless connectors would conventionally be used. For example, the assembly may be used as part of the administration set, for example as part of a Y-set or adapter. The assembly may also be used for devices that provide access to other routes of parenteral administration, such as intraarterial, intramuscular, subcutaneous, intraperitoneal, intrathecal, antravesical, etc.

It will also be recognized that the assembly according to the present disclosure may have one or more advantages relative to conventional devices. For example, the collar and associated barrier is more resistant to inadvertent contamination, because with the collar attached to the device and moveable along the connector, the collar will not be placed on a contaminated surface between uses or come in contact with fingers or other body parts that may contaminate the interior surfaces that contact the needleless connector. Additionally, because the inlet end of the connector passes through the barrier prior to each use, the assembly does not rely solely upon the user remembering to disinfect surfaces prior to use. In fact, the assembly may be used in place of swabbing by the healthcare worker, thereby saving valuable time and reducing the amount of medical waste generated by conventional disinfection protocols that rely upon use of alcohol pads, etc.

We claim:

1. A needleless valve assembly comprising:
a needleless connector including a housing having an inlet end with an inlet opening and an outlet end with an outlet opening, and a valve disposed in the housing to control passage between the inlet opening and the outlet opening,
the valve having a surface disposed in the inlet opening to occlude the inlet opening;
a collar having an exterior surface and an interior surface, and a first end with a collar opening communicating between the interior surface and the exterior surface and a second end with the interior surface of the collar moveably attached to an exterior surface of the housing; and
a barrier disposed across the collar opening with a slit therethrough and including an anti-microbial material,
the collar moveable relative to the housing between a first position with the barrier disposed across the collar opening abutting the inlet end of the housing and the surface of the valve, and a second position with the inlet end of the housing and the surface of the valve depending past the exterior surface of the collar through the slit in the barrier.

2. The needleless valve assembly according to claim 1, wherein the exterior surface of the housing has a threaded section and the interior surface of the collar has a threaded section, the threaded section of the housing engaging the threaded section of the collar.

3. The needleless valve assembly according to claim 1, wherein the housing and the collar have first and second facing surfaces, the needleless valve assembly further comprising a shoe attached to the first facing surface and a race formed in the second facing surface, the shoe being disposed in the race.

4. The needleless valve assembly according to claim 3, wherein the race is aligned with an axis of the housing.

5. The needleless valve assembly according to claim 1, wherein the barrier comprises a single layer including the anti-microbial material.

6. The needleless valve assembly according to claim 1, wherein the barrier comprises two layers, a first layer proximal to the inlet end including the anti-microbial material and a second layer distal to the inlet end.

7. The needleless valve assembly according to claim 6, wherein the second layer is removable from the first layer.

8. The needleless valve assembly according to claim 6, wherein the anti-microbial material comprises one of a chemical disinfectant or a vapor disinfectant.

9. The needleless valve assembly according to claim 8, wherein the first layer comprises a material comprising pores, the anti-microbial material disposed in the pores.

10. The needleless valve assembly according to claim 1, wherein the needleless connector is a Luer-activated valve.

11. A kit comprising:
a needleless valve assembly including:
a needleless connector including a housing having an inlet end with an inlet opening therethrough and an outlet opening, and a valve disposed in the housing to control passage through the inlet opening,
the valve having a surface disposed in the inlet opening to occlude the inlet opening;
a collar having an exterior surface and an interior surface, and a first end with a collar opening and a second end with the interior surface of the collar moveably attached to an exterior surface of the housing; and
a barrier disposed across the collar opening, the barrier having at least one layer of material including an anti-microbial material and a slit,
the collar moveable axially along the housing between a first position with the barrier disposed across the collar opening abutting the inlet end of the housing and the surface of the valve, and a second position with the inlet end of the housing and the surface of the valve depending past the exterior surface of the collar through the slit in the barrier; and
a catheter having a first end attached to the outlet opening of the housing of the needleless connector.

12. The kit according to claim 11, wherein the exterior surface of the housing has a threaded section and the interior surface of the collar has a threaded section, the threaded section of the housing engaging the threaded section of the collar.

13. The kit according to claim 11, wherein the housing and the collar have first and second facing surfaces, the needleless valve assembly further comprising a shoe attached to the first facing surface and a race formed in the second facing surface, the shoe being disposed in the race.

14. The kit according to claim 13, wherein the race is aligned with an axis of the housing.

15. The kit according to claim 11, wherein the barrier comprises a single layer including the anti-microbial material.

16. The kit according to claim 11, wherein the barrier comprises two layers, a first layer proximal to the inlet end including the anti-microbial material and a second layer distal to the inlet end.

17. The kit according to claim 16, wherein the second layer is removable from the first layer.

18. The kit according to claim 16, wherein the anti-microbial material comprises one of a chemical disinfectant and a vapor disinfectant.

19. The kit according to claim 18, wherein the first layer comprises a material comprising pores, the anti-microbial material disposed in the pores.

20. The kit according to claim 11, wherein the needleless connector is a Luer-activated valve.

21. The needleless valve assembly according to claim 1, wherein the antimicrobial material is released onto the inlet end of the housing and the surface of the valve as the collar moves between the first and second positions.

22. The needleless valve assembly according to claim 21, wherein the antimicrobial material is drawn to a surface of the barrier as the collar moves between the first and second positions.

23. The kit according to claim 11, wherein the antimicrobial material is released onto the inlet end of the housing and the surface of the valve as the collar moves between the first and second positions.

24. The kit according to claim 23, wherein the antimicrobial material is drawn to a surface of the barrier as the collar moves between the first and second positions.

* * * * *